United States Patent [19]

Ryan et al.

[11] 4,276,378
[45] Jun. 30, 1981

[54] HIGH SENSITIVITY ASSAYS FOR ANGIOTENSIN CONVERTING ENZYME

[76] Inventors: James W. Ryan, 3420 Poinciana Ave., Miami, Fla. 33133; Alfred Chung, 8781 SW. 87th St., Miami, Fla. 33173

[21] Appl. No.: 854,538

[22] Filed: Nov. 25, 1977

[51] Int. Cl.³ .......................... C12Q 1/38; C12Q 1/36
[52] U.S. Cl. ........................................ 435/23; 435/24; 435/212; 435/219; 424/1.5; 424/2; 260/112.5 R
[58] Field of Search ............... 195/99, 103.5 R, 103.7, 195/114; 260/112.5 R; 424/1, 1.5, 2; 435/23, 24, 13, 212, 219

[56] References Cited

U.S. PATENT DOCUMENTS

| 3,832,337 | 8/1974 | Ondetti et al. | 260/112.5 R |
| 4,137,225 | 1/1979 | Ekenstam et al. | 260/112.5 R |

OTHER PUBLICATIONS

Dorer et al., "Kinetic Properties of Pulmonary Angiotensin-Converting Enzyme, Hydrolysis of Hippurylglycylglycine", Biochim. Biophys. Acta, vol. 429, (1976), pp. 220–228.
Frieland et al., "A Sensitive Fluorimetric Assay for Serum Angiotensin-Converting Enzyme," Am. J. Clin. Path., vol. 66, pp. 416–424.
Cushman et al., "Spectrophotometric Assay and Properties of the Angiotensin-Converting Enzyme of Rabbit Lung," Biochem. Pharm., vol. 20, (1971), pp. 1637–1648.
Chiu et al., "A Sensitive Radiochemical Assay for Angiotensin-Converting Enzyme (Kinnse II)," Biochem. J., vol. 149, (1975), pp. 297–300.
Bakhle, Handbook of Experimental Pharmacology, Page & Bumpus, eds., vol. 37, Springer Verlag, Berlin, (1973), pp. 41–80.
Cheung et al., Biochim. Biophys. Acta, vol. 293, (1973), pp.451–463.
Chushman et al., Experienta, vol. 29, (1973), pp. 1032–1035.
Das et al., J. Biol. Chem., vol. 250, (1975), pp. 6762–6768.
Depierre et al., Enzyme, vol. 19, (1975), pp. 65–70.
Erdos, Am. J. Med., vol. 60, No. 6, (1976), pp. 749–759.
Gavras et al., New Eng. J. Med., vol. 291, (1974), p. 817–821.
Igic et al., Pharmacology and the Future of Man, Proc. 5th Int. Cong. Pharmacology, San Francisco, 1972, vol. 5, (1973), p. 307–319.
Lonzillo et al., Biochem. Biophys. Acta, vol. 491, (1977), pp. 339–344.
Lehninger, Biochemistry, Worth Publishers Inc., New York, (1970), pp. 153–157.
Massey et al., Biochem., vol. 15, (1976), pp. 4906–4918.
Ondetti et al., Science, vol. 196, (1977), pp. 441–443.
Piguilloud et al., Biochem. Biophys. Acta, vol. 206, (1970), pp. 136–142.
Soffer, Ann. Rev.Biochem., vol. 45, (1976), pp. 73–94.
White et al., Principles of Biochemistry, 5th ed., (1973), McGraw-Hill,New York, pp. 589–590 and 939–940.

Primary Examiner—Thomas G. Wiseman

[57] ABSTRACT

A sensitive method for measuring angiotensin converting enzyme in clinical material such as serum, urine, and tissue biopsies. The method employs Hip His Leu as the substrate. The method exploits the finding that sulfate ion in the range of 0.75 through 1.1 M lowers the apparent Km for Hip His Leu from about $2.6 \times 10^{-3}$ M to about $1.8 \times 10^{-4}$ M. This 14-fold decrease in Km effectively permits a more sensitive assay with Hip His Leu. The assay may be fluorimetric or radioactive means to measure the presence of eznymatic reaction.

17 Claims, No Drawings

HIGH SENSITIVITY ASSAYS FOR ANGIOTENSIN CONVERTING ENZYME

RELATED APPLICATION

Co-pending application Ser. No. 795,497, filed May 10, 1977, U.S. Pat. No. 4,115,374, by the inventors herein, discloses novel substrates and a radioassay method for angiotensin converting enzyme in serum.

BACKGROUND

Angiotensin converting enzyme (peptidyl dipeptide hydrolase, hereinafter referred to as ACE) occupies a central role in the physiology of hyptertension. The enzyme is capable of converting the decapeptide angiotensin I, having the sequence AspArgValTyrIleHisProPheHisLeu to an octapeptide, angiotensin II by removal of the carboxyterminal HisLeu. The symbols for various chemical entities are explained in the following table:

TABLE I

Ala = L-alanine
Arg = L-arginine
Asp = L-aspartic acid
Gln = L-glutamine
<Glu = pyro-L-glutamic acid
Gly = glycine
Hip = Hippuric acid (Benzoyl-glycine)
His = L-histidine
Ile = L-isoleucine
Leu = L-leucine
Lys = L-lysine
Phe = L-phenylalanine
Pro = L-proline
Ser = L-serine
Trp = L-tryptophan
Tyr = L-tyrosine
Val = L-valine
ACE = Angiotensin converting enzyme
Bicine = N,N-bis (2-hydroxyethyl) glycine
EDTA = Ethylene diamine tetraacetic acid
Hepes = N-2-hydroxyethylpiperazine-N'-2-ethanesulfonic acid
<HPP = p-hydroxyphenylpropionyl>

Angiotensin I is formed by the action of the enzyme renin, an endopeptidase found in kidney, other tissues and plasma, acting on renin substrate, a serum $\alpha_2$ globulin.

Blood pressure is affected by certain peptides found in the blood. One of these, angiotensin II, is a powerful pressor (blood pressure elevating) agent. Another, bradykinin, a nonapeptide with the sequence ArgProProGlyPheSerProPheArg is a powerful depressor (blood pressure lowering) agent. In addition to a direct pressor effect, angiotensin II stimulates release of aldosterone which tends to elevate blood pressure by causing retention of extracellular salt and fluids. Angiotensin II is found in measurable amount in the blood of normal humans. However, it is found at elevated concentration in the blood of patients with renal hypertension.

The level of ACE activity is ordinarily in excess, in both normal and hypertensive humans, of the amount needed to maintain observed levels of angiotensin II. However, it has been found that significant blood pressure lowering is achieved in hypertensive patients by treatment with ACE inhibitors. (Gavras, H., Brunner, H. R., Laragh, J. H., Sealey, J. E., Gavras, I., and Vukovich, R. A., *New Engl.J.Med.* 291, 817 (1974). The ability to measure variations in the ACE activity in patients under treatment with an ACE inhibitor is therefore of great clinical and research importance. In addition, elevated serum levels of ACE activity have been found to exist in cases of sarcoidosis and also in Gaucher's disease. In some cases of sarcoidosis, serum ACE levels may be more than two standard deviations above the normal mean. In Gaucher's disease, serum levels of enzyme activity may be 60 times higher than those of normals. The elevated blood level seen in active sarcoidosis may fall to the normal range when the disease undergoes spontaneous remission or when therapeutic benefit is achieved through treatment. An effective, simple and convenient assay for the activity of ACE is accordingly a highly desirable tool of great utility to the physician who must deal with this disease, which is not only difficult to diagnose but to monitor.

ACE is a peptidyl dipeptide hydrolase. It catalyzes the hydrolysis of the penultimate peptide bond at the C-terminal end of a variety of acylated tripeptides and larger polypeptides having an unblocked carboxyl group. The peptide hydrolysis is represented diagrammatically as: $R—A_2—A_1 + H_2O \rightarrow R—OH + H—A_2—A_1$, wherein $A_1$ is an amino acid at the carboxyl terminus of the peptide, $A_2$ is an amino acid linked to $A_1$ by a peptide bond, R is an N-substituted amino acid linked to $A_2$ by a peptide bond. The action of ACE results in hydrolytic cleavage of the penultimate peptide bond from the carboxyl-terminal end yielding as reaction products a dipeptide, $HA_2A_1$, and a remnant, $R—OH$.

Several methods for determining ACE activity have been reported in the prior art. The methods may be classified according to whether the dipeptide reaction product or the remnant reaction product is measured. In either case, the reaction product must either be separated from the reaction mixture or treated with a specific reagent to produce a measurable change, for example a color change or a fluorescence.

Methods based upon measurement of the dipeptide reaction product include the following:

(a) The acylated tripeptide HipHisLeu was used as substrate. The dipeptide product HisLeu was measured fluorimetrically following addition of a reagent, o-phthaldialdehyde. The reagent could be used to measure the reaction product in serum without prior separation provided a suitable excess of reagent was added sufficient to form a precipitate with proteins in serum. The fluorescence intensity as a function of HisLeu concentration was nonlinear, therefore, a standard curve was required to calculate the result. Friedland, J., and Silverstein, E., *Am.J.Clin.Path.* 66, 416 (1976). See also, Piquilloud, Y., Reinharz, A., and Roth, M. R., *Biochim.Biophys.Acta* 206, 136 (1970); Depierre, D., and Roth, M., Enzyme 19, 65 (1975). In principle, other fluorescence-inducing agents could be used in place of o-phthaldialdehyde depending on their reactivities with the enzyme reaction products.

(b) The acylated tripeptide HipGlyGly has been employed as substrate in an assay in which the dipeptide reaction product was measured by the ninhydrin reaction. The reaction product was assayed automatically using an automatic analyzer. Dorer, F. E., Kahn, J. R., Lentz, K. E., Levine, M., and Skeggs, L. T., *Biochim.Biophys.Acta.* 429, 220 (1976) (hereinafter referred to as Dorer, et al.).

The following are noteworthy examples of assay methods based upon the measurement of the remnant product:

(a) HipHisLeu was used as substrate, to measure ACE in serum. The remnant reaction product, hippuric acid, was measured spectrophotometrically. The product was first extracted from the acidified reaction mixture with ethyl acetate. However, in order to measure the product in the spectrophotometer it was necessary to evaporate the ethyl acetate to dryness, then redissolve the hippuric acid quantitatively in an aqueous medium. It was necessary to remove all traces of ethyl acetate prior to measurement. Cushman, D. W., and Cheung, H. S., *Biochem.Pharmac.* 20, 1637 (1971).

(b) The above referenced co-pending application, Ser. No. 795,497, discloses an assay in which the substrate is labeled with a radio-active isotope, specifically located in that portion of the substrate molecule destined to become the remnant product of ACE catalyzed hydrolysis.

(c) An extremely sensitive radioassay, using ($^{125}$I) Tyr$^8$-bradykinin as substrate has been described by Chiu, et al., *Biochem.J.* 149, 297 (1975). The assay requires column chromatography and subsequent extensive analysis to identify and quantitate reaction products.

Both the fluorimetric assay and the radioactivity assay are sufficiently sensitive and convenient to make them attractive for the assay of serum ACE. Recently, however, it has been found that ACE occurs in urine, although at greatly reduced levels compared to serum. Using prior art assay methods the urinary protein must be concentrated more than 50-fold before the ACE activity can be measured satisfactorily. A high sensitivity assay for ACE, capable of accurately measuring its activity in urine would be useful for both clinicians and researchers. To the extent that urinary ACE levels correlate with serum levels, the ability to assay ACE in urine will be much more convenient, since it will not be necessary to take a blood sample from the patient. Further, a urinary ACE assay may provide the key to new techniques to monitor renal function as it relates to hypertension. Even more sensitive techniques, capable of detecting ACE levels in small samples of other clinical materials, for example, tissue biopsies, can further expand the scope and power of this valuable diagnostic tool.

The reactivity of the enzyme varies markedly depending on the substrate. At least one type of peptide bond, having the nitrogen supplied by proline, is not hydrolyzed at all. The apparent Michaelis constant (Km) varies from substrate to substrate over several orders of magnitude. For general discussion of the kinetic parameters of enzyme catalyzed reactions, see Lehninger, A., *Biochemistry*, Worth Publishers, Inc., New York, 1970, pp. 153–157. Many peptides which are called inhibitors of the enzymatic conversion of angiotensin I to angiotensin II are in fact substrates having a lower Km than angiotensin I. Such peptides are more properly termed competitive substrates. Examples of competitive substrates include bradykinin, and the peptide BPP$_{5a}$ (also called SQ20475) from snake venom, whose sequence is <GluLysTrpAlaPro.

Numerous synthetic peptide derivatives have been shown to be ACE inhibitors by Ondetti, et al., in U.S. Pat. No. 3,832,337, issued Aug. 27, 1974. The derivatives disclosed therein include chloroacetylPheAlaPro, <GluTrpAlaPro and <GluLysTrpAla. The tripeptide PheAlaPro and its derivative, t-butyloxycarbonyl-PheAlaPro have been reported to inhibit ACE. The compounds were thought to bind competitively with the enzyme, which binding was considered a necessary, but not sufficient, condition for inhibition. Cushman, D. W., Pluscec, J., Williams, N. J., Weaver, E. R., Sabo, E. F., Kocy, O., Cheung, H. S. and Ondetti, M. A., *Experientia* 29, 1032 (1973).

There is extensive documentation in the scientific literature to the effect that ACE requires chloride ions for activity:

Igic, R., Nakajima, T., Yeh, H. S. J., Sorrells, K., and Erdos, E. G., in Pharmacology and the Future of Man, Proc. 5th Int.Cong.Pharmacology, San Francisco, 1972, vol. 5, pp 307–319 (Naragen, Basel 1973) reviewed the field of kininases, including ACE. The authors reported a chloride activating effect for ACE, which varied in amount from substrate to substrate. However, an 86% inhibition of HipHisLeu hydrolysis was reported when chloride was absent.

Das, M. and Soffer, R. L., *J.Biol.Chem.* 250, 6762 (1975) reported the purification of ACE from rabbit lung. The authors used the spectrophotometric assay of Cushman and Cheung using HipHisLeu as substrate. The removal of sodium chloride from the reaction medium resulted in 92% inhibition. The chloride requirement could be met with MgCl$_2$, but not with Na$_2$SO$_4$. The level of Na$_2$SO$_4$ tested was not reported.

Dorer, F. E., Kahn, J. R., Lentz, K. E., Levine, M. and Skeggs, L. T., *Biochim.Biophys.*Acta 429, 220 (1976) reported a kinetic study of the enzyme isolated from hog lung, using HipGlyGly as substrate. Sulfate ion, 0.6 M, was found to be stimulatory in the presence of 0.1 M chloride, at pH 8. Vmax increased about 5-fold and Km decreased about 15%. The effect was considered to be due to increased ionic strength, rather than ion specificity. In the absence of NaCl, there was no hydrolysis of HipGlyGly at any Na$_2$SO$_4$ concentration in the range 0.001 M to 0.6 M.

Cheung, H. S. and Cushman, D. W., *Biochim.Biophys.* Acta 293, 451 (1973), studying ACE inhibition by various synthetic peptides, observed that BPP$_{5a}$, also called SQ20475, having the sequence <GluLysTrpAlaPro, could serve as a substrate for the enzyme. Cleavage of SQ20475 reportedly proceeded more slowly in the presence of chloride than in a buffer of undisclosed composition, presumably lacking chloride.

The repeated observation of chloride ion dependence for maximal ACE activity has prompted some workers to consider such dependence a criterion for the enzyme. See, for example Massey, T. H. and Fessler, D. C., *Biochemistry* 15, 4906 (1976), and Lanzillo, J. J. and Fanburg, B. L., *Biochim.Biophys.*Acta 491, 339 (1977). Unexpected exceptions to the chloride dependence phenomenon have been discovered by the inventors herein, with respect to certain substrates, most notably HipHisLeu, in the presence of sulfate ion. These phenomena have been exploited to provide a high sensitivity assay for ACE. In addition, a novel substrate is described, useful in an extremely sensitive ACE assay method.

For background references see: White, A., Handler, P., and Smith, Ed, *Principles of Biochemistry*, 5th ed., 1973, McGraw-Hill, New York, pp. 589–590, 939–940; Bakhle, Y. S., in *Handbook of Experimental Pharmacology;* I. H. Page and F. M. Bumpus, eds., vol. 37, pp. 41–80, Springer Verlag, Berlin, 1974. Soffer, R., *Ann.Rev.Biochem.* 45, 73 (1976); Erdos, E. G., *Am.J.Med.* 60, (6), 749 (1976).

SUMMARY OF THE INVENTION

Two high sensitivity methods for the measurement of ACE activity in clinical materials such as serum, urine and tissue biopsies, are herein disclosed. Both methods are sufficiently sensitive to measure ACE activity in urine as well as extremely small serum samples.

The first method employs HipHisLeu as substrate. The method exploits the unexpected finding that sulfate ion in the range 0.75–1.1 M lowers the apparent Km for HipHisLeu from about $2.6 \times 10^{-3}$ to about $1.8 \times 10^{-4}$ M. This 14-fold decrease in Km effectively permits a much more sensitive assay than was heretofore possible with HipHisLeu as substrate. The assay may be carried out either by measuring the dipeptide reaction product fluorimetrically, or by measuring the remnant reaction product with substrate specifically radioactively labeled in the Hip moiety.

The second method is ten to twenty times more sensitive than the first. In this method, the novel acylated tripeptide benzoyl PheAlaPro is employed. The substrate has a Km of about $1.4 \times 10^{-5}$ M, which is relatively insensitive to the presence of sulfate. A radioactive label may be incorporated into that portion of the substrate which becomes the remnant product of ACE hydrolysis. A system for selectively extracting the remnant product has been devised. The extremely low Km for benzoylPheAlaPro, coupled with the high sensitivity of radioactivity measurement provides an extremely sensitive assay for ACE.

Such high sensitivity ACE assay methods are useful for measuring ACE levels in urine, thereby enhancing the potential usefulness of ACE measurement as a diagnostic tool. In addition, the assays are sufficiently sensitive to measure serum ACE in extremely small sample quantity, such as could be obtained from a finger prick. Also, where radioactive substrates are employed, the standard serum assay may be carried out with less total substrate. The use of lower total substrate greatly reduces the overall cost of the assay.

DETAILED DESCRIPTION OF THE INVENTION

An assay for ACE, using HipHisLeu as substrate, is herewith described. The assay is more sensitive than any heretofore disclosed using HipHisLeu as substrate. Maximum sensitivity is achieved by the inclusion of sulfate ions, preferably as sodium sulfate, in the reaction mixture. When 0.1 M NaCl is present in the reaction mixture, sulfate ions are stimulatory from 0.1 M to at least 1.1 M. Maximum stimulation occurs in the range from 0.75 M to 1.1 M $Na_2SO_4$. Although the data do not rule out the possibility of trace amounts of chloride contaminating the reaction mixture, in the absence of added chloride ions, $Na_2SO_4$ is stimulatory from about 0.7 M to at least 1.2 M. Surprisingly, reactions carried out in 0.05 M Hepes, pH 8.0, in the absence of added NaCl and in the presence of 0.9 M to 1.2 M $Na_2SO_4$ were faster than reactions carried out in the same buffer containing 0.1 M NaCl and lacking $Na_2SO_4$.

Unexpectedly, in view of the effects reported by Dorer, et al., infra, of sulfate on the ACE catalyzed hydrolysis of HipGlyGly, the Km of HipHisLeu was reduced about 15-fold by the inclusion of 0.75 M $Na_2SO_4$ in a reaction mixture containing 0.1 M NaCl. Furthermore, the effect of sulfate on HipHisLeu hydrolysis is not attributable to ionic strength, as reported for HipGlyGly, since NaCl in the concentration range 0.75 to 1.1 M seriously inhibits the ACE catalyzed hydrolysis of HipHisLeu. In addition, the reaction with HipGlyGly as substrate remains dependent upon the presence of added chloride for activity, whereas the reaction with HipHisLeu can be carried out in the absence of added chloride, if sulfate is present.

The sulfate induced Km lowering for HipHisLeu makes it possible to measure ACE activity with greater sensitivity than has heretofore been possible with HipHisLeu based assay methods. In principle, the sulfate stimulation effect may be employed to improve the sensitivity of any ACE assay using HipHisLeu as substrate. For example, the spectrophotometric assay of Cushman and Cheung, supra, the fluorimetric assay of Silverstein, et al., supra, and the radioactivity assay of Ryan, et al. in U.S. application Ser. No. 795,497 are amenable to sensitivity enhancement by this method. Hip-His-Leu in the concentration of $1 \times 10^{-5}$ M to $2 \times 10^{-3}$ M can be used in the fluorometric assay. The preferred embodiment is the radioactivity assay, described in detail for $^3$H-HipHisLeu in the examples. In that assay, the HipHisLeu concentration may be varied from about $1 \times 10^{-10}$ M up to $2 \times 10^{-3}$ M, depending on the type of reaction kinetics desired, as understood in the art. The preferred concentration range is $10^{-9}$ M to $5 \times 10^{-4}$ M. Other parameters relating to the reaction rate, such as pH, temperature and buffer composition, remain essentially as described in the prior art and may be varied according to well known principles by those skilled in the art, to achieve optimal results. The enhanced sensitivity assays, in particular, the assay method of the preferred embodiment, may be used to measure ACE activity in samples of clinical material such as serum, urine, and tissue samples. Urine contains a dialyzable inhibitor of ACE. Therefore for all references herein to the assay of ACE in urine it is understood that the urine is dialyzed or otherwise treated to remove inhibiting materials.

The behavior of ACE in the sulfate-stimulated assay using HipHisLeu as substrate appears identical with its behavior in prior art assays, with respect to inhibitors. Approximately 50% inhibition was observed in the presence of EDTA, 6 $\mu$M–11 $\mu$M, of dithiothreitol 80 $\mu$M–100 $\mu$M, of angiotensin I, 1 $\mu$M–6 $\mu$M, of bradykinin, 1 $\mu$M–5 $\mu$M, of SQ14225 (D-2-methyl-3-mercaptopropanol-L-proline, Ondetti, M. A., Rubin, B. and Cushman, D. W., Science 196, 441 (1977)), 140 nM–250 nM, and of BPP9a (SQ20881, <GluTrpProArgProGlnIleProPro, Cheung, H. S. and Cushman, D. W., supra), 2 nM–6 nM. Significantly, the enzyme of Guinea pig urine was inhibited by rabbit antibody raised against Guinea pig lung ACE in the sulfate stimulated assay. On the other hand, the same antibody did not significantly inhibit the enzymatic activity of human urine. The foregoing evidence supports the view that the urinary activity measured in the sulfate-stimulated assay is in fact ACE.

Broadly speaking, the discoveries upon which the foregoing new techniques are based make it evident that for each ACE substrate, there will be individually optimal ionic conditions. Certain ion species other than chloride, such as sulfate in the case of HipHisLeu, may be stimulatory or may relieve the chloride dependence, although such stimulation will not exist in every case. For individual substrates, chloride ion may or may not be required and a stimulatory ion may or may not be found. The present findings make it possible to optimize ionic conditions by varying two parameters, the added chloride ion concentration, which may be varied from 0.0 M–1.0 M, and the concentration of the stimulating ion, for example sulfate, which may be varied from zero M to 1.2 M. In this manner, optimal conditions may be found that enhance the sensitivity of prior art assays, as well as assays to be developed in the future. Since the ion effects appear to be substrate-specific, the foregoing optimization step may be employed to enhance the selectivity of ACE measurements, in cases where two substrates or a substrate and an inhibitor are present together.

An even more sensitive assay for ACE activity has been developed using the novel compound $^3$H-benzoylPheAlaPro as substrate. This new substrate can be used to assay ACE in human urine in incubations as short as 15 minutes. The response of this substrate to ions is strikingly different from the response of HipHisLeu. ACE will hydrolyze $^3$H-benzoylPheAlaPro in the absence of any added salt, in 0.05 M Hepes buffer at pH 8.0. As little as 0.01 M added NaCl increases reaction velocity. Added sodium chloride at 0.05 M will increase the apparent reaction velocity approximately 3-fold, but there is little further increase to be obtained by adding additional levels of sodium chloride, up to 0.5 M. In the prior art assay methods measuring the remnant product of HipHisLeu hydrolysis, the reaction is terminated by the addition of dilute hydrochloric acid and the remnant reaction product is extracted therefrom with ethyl acetate, Cushman, D. W. and Cheung, H. S., supra. However, under these conditions, $^3$H-benzoylPheAlaPro is extracted almost quantitatively into ethyl acetate. This difficulty has been solved by the proper choice of extracting solvent. While a variety of organic solvents may be suitable for the extraction step, it is preferred to employ toluene. Approximately 88% of $^3$H-benzoylPhe enters the toluene phase while only 6% of the unhydrolyzed substrate enters the toluene phase, when toluene and the acidified reaction mixtures are in approximately equal volumes at room temperature.

Unlike the previously described assay, sodium sulfate is not stimulatory when $^3$H-benzoylPheAlaPro is used as substrate. The enzyme is active over a broad pH range with a maximum around pH 8.0, but is at least about 50% active in the range pH 7.0–pH 8.8, for both HipHisLeu and benzoylPheAlaPro. Although the enzyme is active in a variety of buffer systems known in the art, it is preferred for convenience, when using benzoylPheAlaPro as substrate, to conduct the assays in 0.05 M Hepes buffer, pH 8.0 containing 0.15 M sodium chloride. Detailed protocols for carrying out the assay are given in the examples. The apparent Km of the reaction of Guinea pig serum ACE with $^3$H-benzoylPheAlaPro is $1.4 \times 10^{-5}$ M. BenzoylPheAlaPro may be used in the concentration range from about $1 \times 10^{-10}$ M to $7 \times 10^{-5}$ M, depending on the kinetic characteristics desired for the reaction, as understood in the art. The preferred concentration range is $1 \times 10^{-9}$ M to $7 \times 10^{-5}$ M.

A comparison of the sensitivity of the disclosed assay methods with each other end with prior art assays may be made by considering assays which depend upon measuring the radioactivity of the remnant reaction product. A prior art assay of this type, using $^3$H-HipGlyGly as substrate has been described (Ryan and Chung, supra). Of the two assays disclosed herein, the sulfate stimulated hydrolysis of $^3$H-HipHisLeu is approximately 20 times more sensitive, and the $^3$H-benzoylPheAlaPro assay is about 10 times more sensitive still. The latter is therefore approximately 200 times more sensitive than the assay using $^3$H-HipGlyGly.

The highly sensitive assay methods disclosed herein are useful in a variety of ways. Their increased sensitivity makes it possible to extend the ability of clinicians and research workers to measure ACE in types of clinical material in which it was not heretofore possible to measure the enzyme, except with great difficulty. In addition to serum, such clinical materials as urine, tissue samples, tissue-cultured cells and the like are amenable to analysis. In addition, conventional analysis in serum can be improved by requiring shorter incubation times and smaller amounts of sample. Where it is desired to use a radioactive substrate, the increased sensitivity makes it possible to use reduced quantities of total substrate, thereby greatly reducing the cost per assay.

EXAMPLES

Example I

Preparation of Guinea pig urine ACE

In all the examples herein, a unit of enzyme is defined as the amount of activity catalyzing the conversion of 1 nmole of substrate per minute per ml using HipGlyGly as substrate.

Guinea pig urine was fractionated using procedures developed previously for the purification of ACE from lung tissue. Dialyzed urine (465 ml, 2,444 milliunits at 8 milliunits/mg of protein) was applied to a column (2.5×7.5 cm) of DEAE-cellulose previously equilibrated with 5 mM Tris-HCl buffer, pH 7.5. Tris is 2-amino-2-hydroxymethyl-1,3-propanediol. The column was washed with 100 ml of the same buffer and then the enzyme was eluted as a narrow peak by adding sodium chloride to 0.3 M. The active fraction (3.7 ml, 970 milliunits at 66 milliunits/mg of protein) was applied to a column (1.2×50 cm) of Sephadex G-100 (Trademark of Pharmacia Chemical Co., Uppsala, Sweden) in 10 mM ammonium acetate buffer, pH 7.5. The enzyme activity eluted in the void volume (5.0 ml, 1,100 milliunits at 814 milliunits/mg of protein. The final product was judged to be approximately 8%–13% pure on the bases of analytical results obtained by disc-gel electrophoresis and by comparision with pure angiotensin converting enzyme obtained from Guinea pig lung.

An alternative enzyme purification procedure has been developed. Collected urine was centrifuged briefly to remove particulate matter, then concentrated by ultrafiltration, using an ultrafiltration membrane which retains molecules greater than 10,000 molecular weight. One liter of urine was concentrated to 20–30 mls, then reconstituted with water to the original volume. Three cycles of ultrafiltration were carried out in this manner and the final concentrated protein was applied to a DEAE cellulose column, as previously described. The column was eluted with a linear gradient from 0 M to 0.4 M NaCl in 5 mM tris-HCl buffer, pH 7.5. The active fractions were again concentrated by ultrafiltration, reconstituted in 1 mM sodium phosphate, pH 7.0 containing 0.1% (w/v) Triton x-100 (Trademark, Rohm and Haas, Corp., Philadelphia, Pa). The protein was reconcentrated, and applied to a hydroxylapatite column 2.5 cm×7.5 cm equilibrated in the same buffer. The column was eluted with a gradient of sodium phosphate, pH 7, from 1 mM–10 mM. The chromatography of hydroxylapatite was carried out in the cold, for example at 4° C. Active fractions were again concentrated by ultrafiltration and applied to a Sephacryl SS200 (Trademark, Pharmacia Chemical Co., Uppsala, Sweden), 2.5 cm×110 cm, in 0.1 M tris-HCl, pH 7.5. Upon elution with the same buffer, the enzyme was found in fractions just after the void volume had passed through the column. On the bases of activity measurements, the preparation obtained by this procedure was judged to be about 13% pure.

EXAMPLE 2 p-I-Hip-His-Leu

A solution of 30.5 mg (0.1 mmol) of p-I-hippuric acid (p-I-benzoyl-glycine) and 11.5 mg (0.1 mmol) of N-OH-succinimide in tetrahydrofuran were reacted in a cool solution of 24.7 mg (0.12 mmol) of dicyclohexylcarbodiimide in tetrahydrofuran at about 0° C. The reaction mixture was stirred in an ice bath for 1 hour and then at room temperature overnight. Dicyclohexylurea was removed by filtration and the solvent from the filtrate was removed with a rotary evaporator. A suspension of 32.2 mg (0.12 mmol) of His-Leu and 8.4 mg (0.1 mmol) of sodium bicarbonate in Dimethylformamide and water, equal parts by volume, were cooled in an ice bath. A cool solution of p-I-hippuryl-N-OH-succinimide ester in 1 ml of dimethylformamide was added with stirring. The reaction mixture was stirred in an ice bath for 1 hour and then at room temperature overnight.

Solid material was removed by filtration and the solvents from the filtrate were removed on a rotary evaporator under high vacuum at 35° C. Water was added to the residue and the pH was adjusted to pH 4 with 0.1 N hydrochloric acid. The aqueous solution was extracted 3 times with ethyl acetate. Water from the aqueous solution was removed with a rotary evaporator under high vacuum at 35° C. The crude peptide was purified by CM-Sephadex (Trademark, Pharmacia Chemical Co., Uppsala, Sweden) column chromatography (elution with 0.1 M acetic acid buffered to pH 6.0 with ammonium hydroxide). The peptide behaved as a single substance on examination on paper electrophoresis at pH 2 and pH 5. Similarly, it behaved as a single substance in 3 thin layer chromatography systems. The final product was reactive with Pauly reagents and o-tolidine/chloride reagents.

$^3$H-HipHisLeu

The product, p-I-HipHisLeu was treated by catalytic tritiation with 10 curies $^3$H$_2$ gas at one atmosphere for 1 hour in the presence of 5% Rhodium on calcium carbonate in dimethylformamide-water, equal parts by volume. The dehalogenated, tritiated product $^3$H-HipHisLeu, with tritium incorporated in the Hip moiety, was purified by partition chromatography.

EXAMPLE 3

Sulfate and Chloride Effects $^3$H-HipHisLeu prepared as described in Example 2 and $^3$H-benzoylPheAlaPro, prepared as described in Example 5, were used as substrates for Guinea pig urinary ACE, prepared as described in Example 1. In all experiments, the buffer was 0.05 M Hepes, pH 8.0, containing added salts, as indicated. All incubations were carried out at 37° C. for 10 minutes. Enzyme was diluted in the reaction buffer to provide not more than 15% hydrolysis during the 10 minute incubation. Enzyme, 50 µl, was mixed with 50 µl $^3$H-Hip-HisLeu, 0.2 mM, having 150,000 total counts per minute (cpm), or with $^3$H-benzoylPheAlaPro having 100,000 cpm to 200,000 cpm. Reactions were carried out in the presence of 0.1 M NaCl or in the absence of NaCl, with varying amounts of Na$_2$SO$_4$ added. The results are shown in Table 1.

TABLE 1

| Na$_2$SO$_4$ concentration | Reaction Velocity-Percent of Substrate Hydrolyzed in 10 minutes | | |
|---|---|---|---|
| | HipHisLeu | | benzPheAlaPro |
| | 0.05M Hepes, pH 8.0 0.0M NaCl | 0.05M Hepes, pH 8.0 0.1M NaCl | 0.05 Hepes, pH 8.0 0.15M HCl |
| 0 | 0 | 0.3 | 4.4 |
| 0.1 | 0 | — | 5.0 |
| 0.2 | 0 | — | 4.45 |
| 0.3 | 0 | — | 4.85 |
| 0.4 | 0.1 | 4.1 | — |
| 0.5 | 0.1 | — | 5.6 |
| 0.6 | 0.25 | 8.3 | — |
| 0.7 | 0.25 | — | — |
| 0.75 | 0.25 | 12.05 | — |
| 0.8 | 0.25 | — | — |
| 0.9 | 0.7 | 12.25 | — |
| 1.05 | — | — | — |
| 1.2 | 3.9 | — | — |

EXAMPLE 4

Kinetics of Sulfate-Stimulated HipHisLeu Hydrolysis

The apparent Km of $^3$H-HipHisLeu, prepared as described in Example 2 was carried out in a reaction buffer composed of 0.05 M Hepes, pH 8.0, 0.1 M NaCl and 0.75 M Na$_2$SO$_4$. In each assay, 50 µl of Guinea pig serum diluted 1–20 (v/v) in the reaction buffer was mixed with 50 µl of buffer containing sufficient $^3$H-HipHisLeu to provide approximately 100,000 cpm total, together with sufficient unlabeled HipHisLeu to produce the desired substrate concentrations, as indicated in Table 2. Enzyme and substrate were incubated for 10 minutes at 37° C., at which time 1 ml of 0.1 M HCl was added to stop the reaction. The reaction mixture was then extracted with 1 ml ethyl acetate. 500 µl of the ethyl acetate fraction was sampled and counted in a scintillation counter. The data are shown in Table 2. When plotted by the method of Lineweaver and Burke (See Lehninger, supra,) a Km value of $1.77 \times 10^{-4}$ M was obtained.

TABLE 2

| S (HipHisLeu Concentration) mM | 1/S mM$^{-1}$ | V (reaction velocity) nmoles · min$^{-1}$ · ml$^{-1}$ | 1/V nmole$^{-1}$ · min · ml |
|---|---|---|---|
| 0.08 | 12.5 | 1.76 | 0.57 |
| 0.07 | 14.3 | 2.14 | 0.47 |
| 0.06 | 16.7 | 1.28 | 0.78 |
| 0.05 | 20.0 | 1.14 | 0.88 |
| 0.04 | 25.0 | 1.28 | 0.78 |
| 0.03 | 33.3 | 0.74 | 1.35 |
| 0.02 | 50.0 | 0.52 | 1.92 |
| 0.01 | 100.0 | 0.30 | 3.33 |

Km = $1.77 \times 10^{-4}$ M
V$_{max}$ = 5.59 nmoles · min$^{-1}$ · ml$^{-1}$

EXAMPLE 5

Synthesis of H-Ala-Pro-benzyl ester.HCl

A solution of 8.46 g (35 mmol)of H-Pro-benzyl ester.HCl in tetrahydrofuran was neutralized with 4.75 ml (35 mmol) of N-ethyl morpholine in an ice water bath at about 0° C. The resulting solution was then reacted with 8.59 g (30 mmol) of t-butyloxycarbonyl-Ala-N-OH-succinimide ester in tetrahydrofuran (with stirring) at about 0° C. for 1 hour. The reaction mixture was slowly warmed to room temperature and was allowed to stand overnight. Solvent was removed with a rotary evaporator. Ethyl acetate was added to the residue, which was then washed with a succession of solutions: saturated sodium chloride, cold 0.1 M hydrochloric acid, saturated sodium chloride, 1 N sodium bicarbonate and again with saturated sodium chloride. The organic phase was dried over anhydrous magnesium sulfate and was then filtered. An oily product resulted upon solvent removal (8.3 g; 75.5% yield). (Amino acid analysis: Ala 1.14, Pro 1.00) Crude product (2.20 g) was deprotected with a solution of anhydrous hydrogen chloride in tetrahydrofuran at 0° C. for 1 hour. Anydrous ether was added and the product was recovered by filtration. Crystallization from ethanol, benzene and hexane yielded 1.96 g of white crystals; melting point 156°–158° C. The product appeared to be hydroscopic. The product moved towards the cathode on electrophoresis at pH 5, and behaved as a single substance in six thin layer chromatography systems. The product was reactive with ninhydrin and with O-tolidine/$Cl_2$ reagents.

Synthesis of p-I-benzoyl-Phe-Ala-Pro-benzyl ester

A solution of 110 mg (0.35mmol) of H-Ala-Pro-benzyl ester.HCl in redistilled dimethylformamide was neutralized with 0.049 ml of triethylamine (0.35 mmol) at about 0° C. A cool solution of 148 mg (0.3 mmol) of p-I-benzoyl-Phe-N-OH-succinimide ester in dimethylformamide was added dropwise with stirring. The reaction mixture was stirred in an ice bath for 1 hour and then at room temperature overnight. Further work up of the reaction product proceeded as described for t-butyloxycarbonyl-Ala-Pro-benzyl ester. The resulting material was homogeneous in six thin layer chromatography systems and behaved as a neutral peptide on electrophoresis at pH 5. The product was not reactive with ninhydrin but was reactive with the O-tolidine/$Cl_2$ reagents.

Synthesis of p-I-benzoyl-Phe-Ala-Pro-OH

A solution of 75 mg (0.1 mmol) of p-I-benzoyl-Phe-Ala-Pro-benzyl ester in 0.3 ml of anhydrous methanol was saponified with 0.3 ml of 1 M potassium hydroxide in methanol at room temperature for 24 hours. Water was added and the aqueous solution was extracted 3 times with ethyl acetate. The aqueous solution was cooled and then acidified to pH 2 with 1 M hydrochloric acid. The product was then recovered by extraction with ethyl acetate. The product was purified by DEAE Sephadex A-25 (Trademark, Pharmacia Chemical Co., Uppsala, Sweden) eluted with 0.2 M ammonium acetate buffer, pH 8.6. The product behaved as a single substance in 5 thin layer chromatography systems. It was not reactive with ninhydrin but was reactive with O-tolidine/$Cl_2$ reagents.

Synthesis of benzoyl-Phe-Ala-Pro (catalytic dehydrogenation of p-I-benzoyl-Phe-Ala-Pro The halogenated compound was treated by catalytic hydrogenation with $H_2$ gas at 39 lb/square inch (absolute), for 1 hour, over 5% Rhodium on calcium carbonate in dimethylformamide and water, 1:1 (v/v). The dehalogenated product was purified by partition chromatography (Sephadex G-25 developed with n-butanol, acetic acid and water, 4:1:5). Tritiation was performed similarly but with 10 curies of $^3H_2$-gas at one atmosphere for 1 hour. The radioactive product was $^3H$-labeled in the benzoylPhe moiety of benzoyl-PheAla-Pro.

EXAMPLE 6

Kinetics of Benzoyl-Phe-Ala-Pro Hydrolysis

The apparent Km for the ACE catalyzed hydrolysis of benzoyl-Phe-Ala-Pro was measured in the following manner. The reaction buffer was 0.05 M Hepes, pH 8.0, containing 0.15 M NaCl. Guinea pig serum was diluted 1:1000 to provide the enzyme. A mixture of 50 µl diluted serum and 50 µl of substrate, diluted in the reaction buffer to provide the appropriate substrate concentration for each experiment, was incubated at 37° C. for 10 minutes. At the end of the incubation, 1.0 ml of 0.1 M HCl was added to stop the reaction. The reaction mixture was then extracted with 1.0 ml toluene, and a 0.5 ml aliquot of the toluene phase was counted in a scintillation counter. The data are shown in Table 3. When plotted according to the method of Lineweaver and Burke, (See Lehninger Supra,) an apparent Km of $1.4 \times 10^{-5}$ M was obtained.

TABLE 3

| S BenzPheAlaPro concentration µM | 1/S µM$^{-1}$ | V reaction velocity pmole . min$^{-1}$ . ml$^{-1}$ | 1/V pmole$^{-1}$ . min . ml |
|---|---|---|---|
| 1.0 | 1.000 | 0.67 | 1.50 |
| 5.0 | 0.200 | 2.08 | 0.48 |
| 10.0 | 0.100 | 4.17 | 0.24 |
| 66.7 | 0.015 | 9.09 | 0.11 |

$Km = 1.4 \times 10^{-5}$ M
$V_{max} = 10$ pmole . min$^{-1}$ . ml$^{-1}$

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for measuring the activity of angiotensin converting enzyme in a sample of clinical material, comprising:
   diluting said sample in a buffer comprising a stimulatory amount of sulfate ion, where said sulfate ion is in the concentration range of 0.1 M–1.1 M and stimulates the angiotensin converting enzyme hydrolysis of HipHisLeu;
   adding sufficient HipHisLeu to the buffer-diluted sample to provide a reaction mixture having a concentration of HipHisLeu prior to incubation in the range of $1 \times 10^{-10}$ M $-2 \times 10^{-3}$ M;

incubating the reaction mixture for a time sufficient to permit a measurable reaction to occur; and, measuring the amount of HisLeu produced by angiotensin converting enzyme catalyzed hydrolysis of HipHisLeu.

2. A method as in claim 1 wherein the sample of clinical material is urine.

3. A method according to claim 1 wherein the HipHisLeu concentration is in the range $1 \times 10^{-9}$ M $-5 \times 10^{-4}$ M.

4. A method according to claim 1 wherein the sulfate ion concentration is in the range of 0.7 M to 1.1 M.

5. A method according to claim 1 wherein the buffer contains 0.1 M chloride ions.

6. A method according to claim 1 wherein the step of measuring the HisLeu comprises adding a fluorescence—inducing agent, then measuring the fluorescence intensity which is a function of the concentration of the HisLeu reaction product.

7. A method according to claim 1 wherein the HipHisLeu concentration is in the range from $1 \times 10^{-5}$ M to $2 \times 10^{-3}$ M, the sulfate concentration is 0.75 M, the buffer contains 0.1 M chloride ions, and the step of measuring the HisLeu comprises adding o-phthaldialdehyde and measuring the fluorescence intensity which is a function of the concentration of the HisLeu.

8. A method for measuring the activity of angiotensin converting enzyme in a sample of clinical material, comprising:

providing a reaction buffer comprising a stimulatory amount of sulfate ion, where said sulfate ion is in the concentration range of 0.1 M–1.1 M and stimulates the angiotensin converting enzyme hydrolysis of HipHisLeu;

mixing said sample together with HipHisLeu in the reaction buffer to provide a reaction mixture, the HipHisLeu having a final concentration in the range of $1 \times 10^{-10}$ M $-2 \times 10^{-3}$ M;

incubating the reaction mixture in order to permit an angiotensin converting enzyme catalyzed reaction to proceed to a measurable extent;

stopping the reaction by acidifying the reaction mixture; and, measuring the amount of Hip produced by angiotensin converting enzyme catalyzed hydrolysis of HipHisLeu.

9. A method according to claim 8 wherein the concentration of HipHisLeu is in the range from $1 \times 10^{-9}$ M to $5 \times 10^{-4}$ M.

10. A method according to claim 8 wherein the sulfate ion concentration is in the range of 0.7 M to 1.1 M.

11. A method according to claim 8 wherein the reaction buffer contains 0.1 M chloride ions.

12. A method according to claim 8 wherein at least a portion of the HipHisLeu molecules are radioactively labeled in the Hip moiety, the Hip produced by angiotensin converting enzyme catalyzed hydrolysis of HipHisLeu is separated from the HisLeu produced by said hydrolysis and unreacted HipHisLeu in the reaction mixture, and the radioactivity of the Hip is measured in order to measure the activity of any angiotensin converting enzyme present in said sample.

13. A method according to claim 8 wherein the HipHisLeu concentration is in the range of $1 \times 10^{-9}$ M $-5 \times 10^{-4}$ M, the sulfate ion concentration is 0.75 M, the reaction buffer contains 0.1 M chloride ion, at least a portion of the HipHisLeu molecules are radioactively labeled in the Hip moiety, and after stopping the reaction the Hip produced by angiotensin converting enzyme catalyzed hydrolysis of HipHisLeu is separated from the HisLeu produced by said hydrolysis and unreacted HipHisLeu in the reaction mixture and the radioactivity of the Hip is measured in order to measure the activity of any angiotensin converting enzyme in said sample.

14. A method according to claim 13 wherein the clinical material is urine.

15. A method for measuring angiotensin converting enzyme activity in a sample of clinical material comprising:

providing HipHisLeu as the substrate for angiotensin converting enzyme;

providing a buffer adjusted for optimal angiotensin converting enzyme activity, said buffer containing added chloride ion to provide a final concentration in the range of 0.0 M–1.0 M and also containing an added stimulatory sulfate ion to provide a final concentration in the range of 0.1 M–1.1 M, said sulfate ion stimulates the angiotensin converting enzyme hydrolysis of HipHisLeu;

producing a reaction mixture by mixing together the substrate and said sample in the buffer;

incubating the reaction mixture to permit an angiotensin converting enzyme catalyzed reaction to occur; and, measuring the amount of any reaction product produced by angiotensin converting enzyme catalyzed hydrolysis of HipHisLeu.

16. A method according to claim 15 wherein the concentration of chloride ion is 0.0 M and the concentration of sulfate ion is in the range of 0.75 M–1.1 M.

17. A method according to claim 15 wherein the concentration of chloride is 0.1 M.

* * * * *